United States Patent [19]

Brown et al.

[11] Patent Number: 5,011,378
[45] Date of Patent: Apr. 30, 1991

[54] PUMP TUBE MOUNT AND CARTRIDGE FOR INFUSION PUMP

[75] Inventors: Eric W. Brown, Newport Beach; Charles M. Kienholz, San Dimas, both of Calif.

[73] Assignee: I-Flow Corporation, Irvine, Calif.

[21] Appl. No.: 301,628

[22] Filed: Jan. 24, 1989

Related U.S. Application Data

[63] Continuation-in-part of Ser. No. 216,512, Jul. 8, 1988, Pat. No. 4,950,245.

[51] Int. Cl.$^5$ ............................................. F04B 43/12
[52] U.S. Cl. ................................... 417/360; 417/474; 417/475
[58] Field of Search .................... 417/360, 474–480; 604/131; 248/68.1

[56] References Cited

U.S. PATENT DOCUMENTS

| | | | |
|---|---|---|---|
| 2,412,397 | 12/1946 | Harper | 417/474 |
| 3,778,195 | 12/1973 | Bamberg | 417/479 X |
| 4,142,524 | 3/1979 | Jassawalla, et al. . | |
| 4,340,153 | 7/1982 | Spivey . | |
| 4,391,600 | 7/1983 | Archibald | 417/478 X |
| 4,397,639 | 8/1983 | Eschweiler et al. . | |
| 4,479,761 | 10/1984 | Bilstad et al. | 417/479 X |
| 4,479,797 | 10/1984 | Kobayashi et al. . | |
| 4,493,704 | 1/1985 | Beard et al. . | |
| 4,650,469 | 3/1987 | Berg et al. . | |
| 4,696,671 | 9/1987 | Epstein et al. . | |
| 4,741,736 | 5/1988 | Brown . | |
| 4,756,706 | 7/1988 | Kerns et al. . | |
| 4,890,984 | 1/1990 | Alderson et al. | 417/479 |

FOREIGN PATENT DOCUMENTS

| | | | |
|---|---|---|---|
| WO8101728 | 6/1981 | PCT Int'l Appl. | 417/476 |
| WO8911302 | 11/1989 | PCT Int'l Appl. | 417/474 |

*Primary Examiner*—Leonard E. Smith
*Assistant Examiner*—Eugene L. Szczecina, Jr.
*Attorney, Agent, or Firm*—Robert M. Asher

[57] ABSTRACT

An infustion pump fluid source cartridge having a pump interface portion and a fluid source portion. The top edge of the cartridge is bevelled in the fluid source portion to permit bending of the fluid source portion to securely position the pump interface portion against the pump without distorting the pump interface portion. A pump tube mount is provided for insertion into such cartridge. The pump tube mount includes a uniquely shaped front wall and a rear wall which extends downward in order to butt up against a ledge. Tabs extend from the rear wall in order to snap into an opening beneath the ledge. A compressible tube is mounted in the tube mount by providing a cylindrical fitting having an indentation. The tube may be held in the indentation by a collar surrounding the tube in alignment with the indentation.

17 Claims, 7 Drawing Sheets

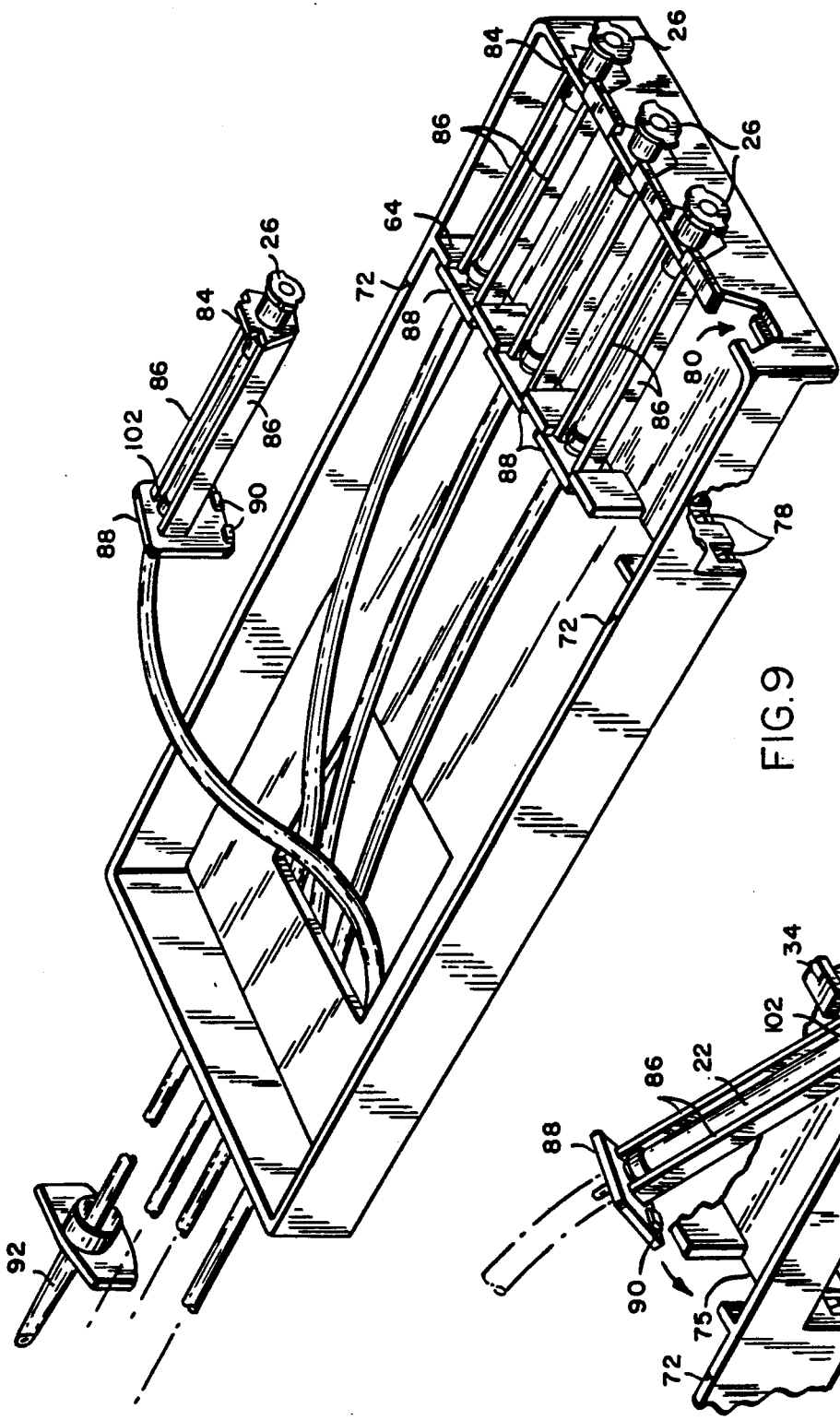

PUMP TUBE MOUNT AND CARTRIDGE FOR INFUSION PUMP

This is a continuation-in-part of U.S. patent application Ser. No. 216,512, filed July 8, 1988 now U.S. Pat. No. 4,950,245.

BACKGROUND OF THE INVENTION

This invention relates to a fluid source cartridge and a pump tube mount insertible into the cartridge.

It is an object of this invention to provide a cartridge and tube mount which accurately position a tube within an infusion pump to permit the automatic delivery of fluid at a precisely determined rate. It is desirable that such accuracy be obtained using low cost plastic pieces.

When a cartridge is inserted into a peristaltic pump, the pumping fingers must interact with the pump tube mounted in the cartridge to open and close the tube completely Any warping of the cartridge or any mispositioning of the tube may permit a leak when a finger is depressed against the tube Any such leak would result in an inaccurate infusion rate. Therefore, it is desirable that a cartridge and pump tube mount be provided which accurately positions the pump tube in three dimensions.

The pump tube used in an infusion pump cartridge is preferably made from a compressible material which is inert with respect to the fluids to be delivered through the tube. Such an inert, compressible material very often does not bond well with adhesives. Thus, in attaching such a tube to a plastic mount, a common method was to provide a fitting with pointed ridges projecting therefrom. The ridges would dig into the inner circumference of the tube and hold it in place. This has the disadvantage of possibly tearing the tube material. It is an object of the present invention to provide a mount for such a tube which does not subject the tube to tearing forces.

SUMMARY OF THE INVENTION

The present invention is directed to a fluid source cartridge and pump tube mount insertible into the cartridge. The tube mount features an elongated fitting having a cylindrical exterior portion and an indentation such as an angular groove about said exterior portion. A tube of compressible material is mounted on the fitting such that the exterior portion of the fitting makes surface contact with the inner surface of the tube. A collar surrounds the tube at the indentation. The collar can thus force the inner circumference of the tube into the indentation to securely hold the tube on the fitting.

The pump tube mount secures the tube between a front wall and a rear wall. A rigid base is located beneath the tube to support the tube against the pressure of the peristaltic pump fingers. The rear wall extends downwards and has tabs extending therefrom so that the mount snaps into place when the mount is properly installed into the cartridge. The tabs secure the mount in place, once properly installed. The front wall of the tube mount is uniquely shaped to match the shape of an opening in the cartridge. This advantageously helps to insure that the proper mounts are being used in the cartridge and to precisely locate the mount in the cartridge.

The fluid source cartridge itself is a housing with two end walls connected by two side walls. The side walls have a top edge which form a fulcrum between the portion of the cartridge bearing the tube mounts and the remainder of the cartridge. Thus, advantageously when the cartridge is locked onto the pump, rather than bowing the entire cartridge causing inaccuracy in the relative position between the pump fingers and the tube, bending is substantially limited to the portion of the cartridge behind the fulcrum away from the tube mount section. The present invention advantageously provides modularity such that the cartridge may support any number from one to four fluid sources, it being only necessary to provide the appropriate number of pump tube mounts in the cartridge.

Other objects and advantages of the present invention will become apparent during the following description of the presently preferred embodiment of the invention taken in conjunction with the drawings.

DETAILED DESCRIPTION OF THE DRAWINGS

FIG. 9 is a perspective view of a cartridge of the present invention along with the pump tube mounts of the present invention.

FIG. 10 illustrates how a pump tube mount of the present invention is inserted into the cartridge of the present invention.

DETAILED DESCRIPTION OF THE PREFERRED EMBODIMENTS

Figure 1:
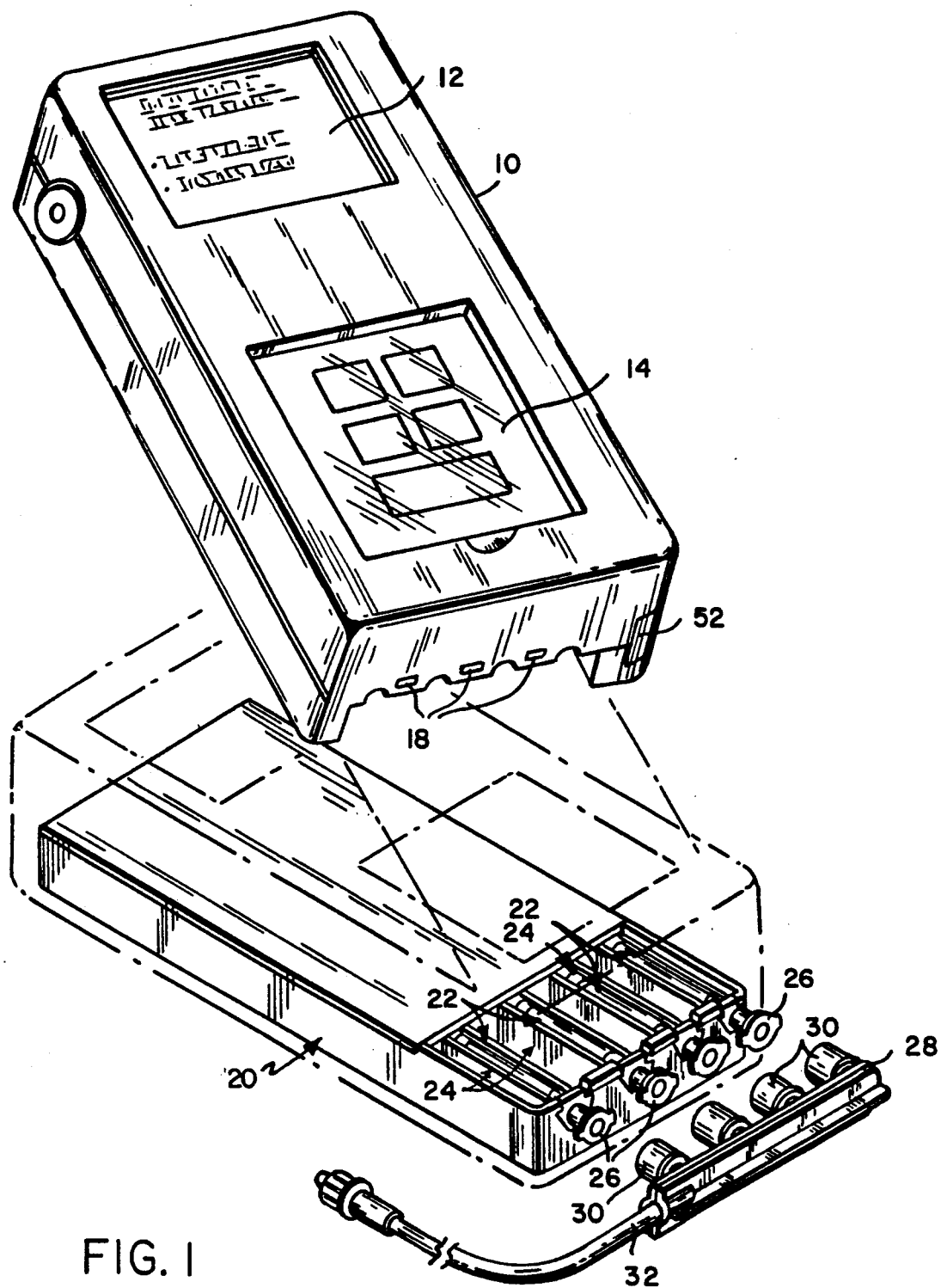
FIG. 1 is an isometric view of a pump with a cartridge of the present invention.
Figure 4:
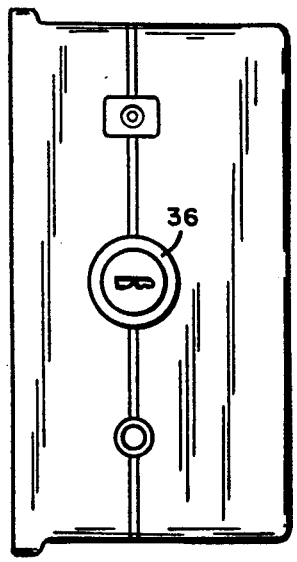
FIG. 4 is an end view of the pump of FIG. 3.

Referring now to FIG. 1, a pump housing 10 is provided for pumping fluid from a multiple fluid cartridge 20. The pump housing 10 is provided with a liquid crystal display 12, a keyboard 14 and as shown in FIG. 4, programming jack 16. The underside of the pump housing 10 forms a cavity for receiving the cartridge 20. The cavity extends through one end of the pump housing 10. At the open end of the housing, there are several cartridge retaining holes 18 for engaging tabs 34 on the cartridge.

The cartridge 20 houses one or more pump tube mounts 24. Each pump tube mount 24 is connected to a fluid source which is either stored in a bag or a pouch in a fluid source portion of the cartridge or stored on a bag hanging from an intravenous delivery pole. To connect with a bag hanging from a pole, the cartridge's fluid source portion may have a window through which lumens may be inserted to connect the bag with the tube mount. Each pump tube mount 24 includes a compressible tube 22 made from a material which is inert to the fluids which will be fed through the tube. At the outer end of the pump tube mount 24, a luer connector 26 serves as the outlet for delivering fluid into an output lumen.

Individual output lumens may be connected to each of the luer connectors 26. These lumens may remain separate or they may be fused together to form a multilumen tube for outputting the fluid to a connector for making connection with an implanted catheter, for example. The multilumen output tube may be connected to any of a variety of multilumen connectors. Three types of multilumen connectors are shown in the co-pending parent U.S. patent application Ser. No. 216,512, filed on July 8, 1988 owned by the same assignee as the present invention. The disclosure of said parent application is hereby incorporated by reference herein. A needle connector 28 may be used in which each lumen is connected to a hollow injection needle. The needle connector may be inserted through a silicone block to make connection with a connector for a multilumen catheter. Another option is a multilumen connector such as that described in co-pending U.S. patent application Ser. No. 178,673 filed on Apr. 7, 1988, owned by the same assignee as the present invention. The disclosure of said application is hereby incorporated by reference herein. A third possibility for the multilumen output tube is to connect each lumen separately to a luer connector so that individual connections can be made to four separate catheter lines.

An alternative connector for delivering fluids from the cartridge to a patient may be a single lumen manifold 28 as shown in FIG. 1. The manifold 28 can be provided with four connectors 30 for securely attaching to the luer connectors 26, extending from the cartridge. Each of these connections may then lead to a single lumen 32. When this type of connector is used, it is normal practice to make the fluid source furthest from the manifold output a flushing solution With this arrangement, the pump generally delivers one solution at a time or one fluid in conjunction with the flushing solution Before switching from one solution to another, the flushing solution is delivered to clean out the single lumen so as to prevent intermixing of different fluid solutions. This would be necessary in the case of drugs which are either incompatible or which cause precipitation when mixed.

Figure 2:
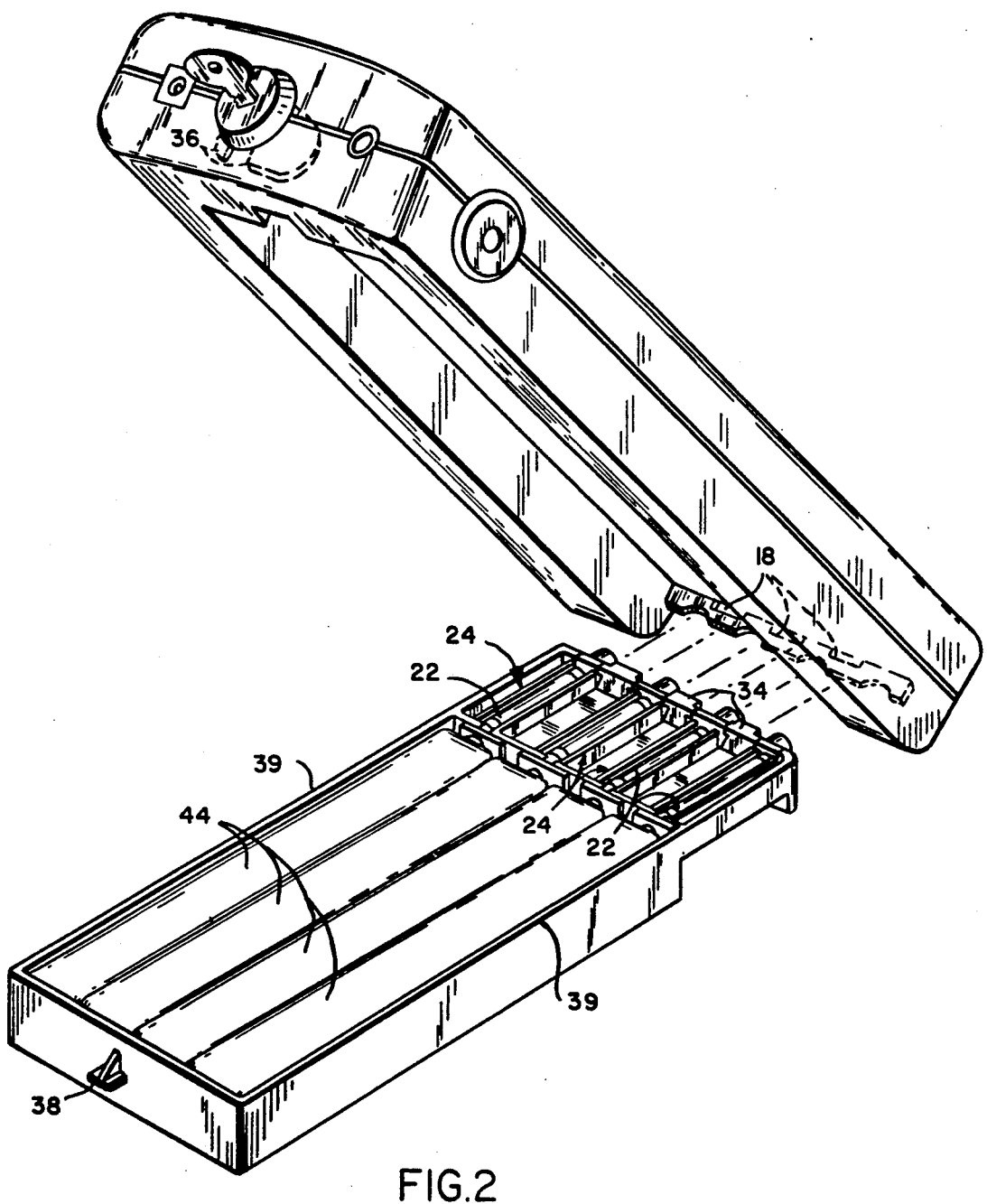
FIG. 2 is a second isometric view of the cartridge of the present invention illustrating its relationship with a pump.

The cartridge 20 is provided with several positioning tabs 34 which extend from the front end of the cartridge. The tabs 34 are inserted into the holes 18 in the pump as shown in FIG. 2. The engagement of the tabs 34 with the holes 18 precisely positions one end of the pump interface portion of the cartridge 20 with respect to the pump 10.

Moreover, by providing at least three tabs 34 spread across the front end of the cartridge, the cartridge is supported across its entire width and bowing of the cartridge is avoided. A cartridge 20 of the present invention is preferably used with a pump having a key operated latch 36. The lock 36 engages a tab 38 extending from the rear end of the cartridge 20. As will be discussed below in greater detail with respect to FIGS. 6–8, the cartridge 20 has the top edge 39 which forms a fulcrum 72 at the rear of the pump tube mounts. The top edge 39 is bevelled from the fulcrum 72 near the rear of the pump tube mounts down to the rear end of the cartridge 20. When the cartridge 20 is inserted it must be pushed up against the pump. The latch 36 engages the tab 38 to lock the cartridge in a pushed up position providing tension in the cartridge 20. Advantageously, in accordance with the present invention, by locating the fulcrum of the top edge behind the pump interface portion carrying the pump tube mounts, the bending of the cartridge is substantially restricted between the fulcrum and the rear end of the cartridge 20. The tension provided by the lock provides a repeatable position for an inserted cartridge and the fulcrum ensures that the entire pump interface portion is secured flat against the pump. This is an important feature since if the cartridge were permitted to bow away from the pump in the pump interface portion, it is possible that one of the pump fingers would not fully close off a pump tube as required to provide precision infusion rates.

FIG. 2 illustrates flexible pouches 44 used as the fluid sources within the cartridge 20. Each fluid source pouch 44 is connected to a pump tube mount 24. At present, the following procedure is suggested for using the cartridges 20 when it is provided with empty pouches 44. The desired fluid is injected into the connector outlet 26, using a syringe or other conventional means. After filling the pouch 44 with the desired amount of fluid, the connector outlet 26 is attached to the output line. When all of the pouches are filled with their fluid, the cartridge may be inserted into the pump housing 10 and a purge cycle may be run on each of the fluid sources to pump out all of the air which may have gotten into the pouch or pump tube. After purging the air, the cartridge 20 is ready for use in an infusion.

Figure 3:
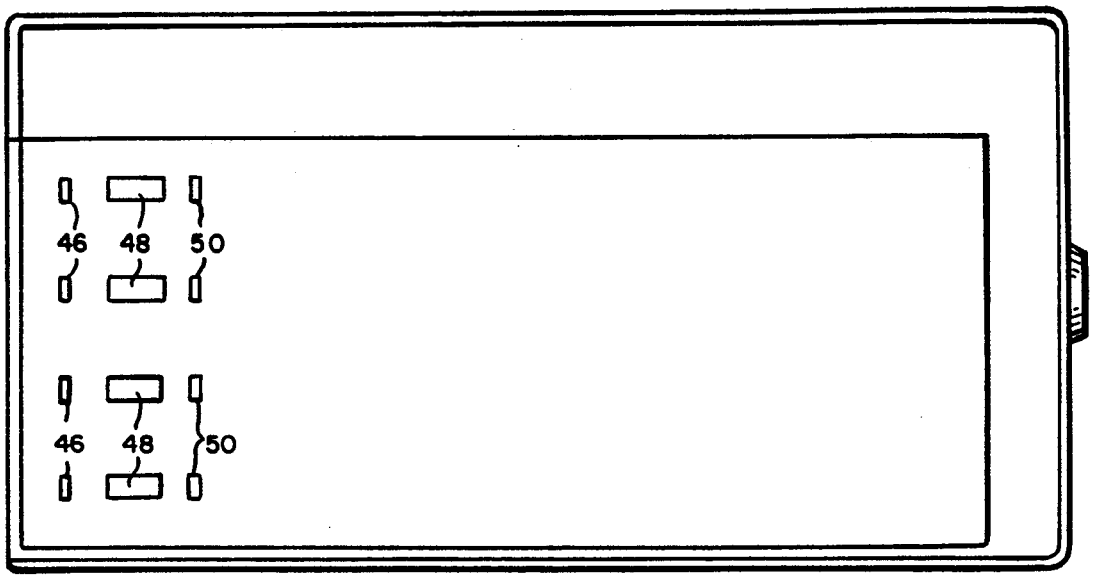
FIG. 3 is a bottom plan view of a pump for use with the present invention without the cartridge in place.
Figure 5:
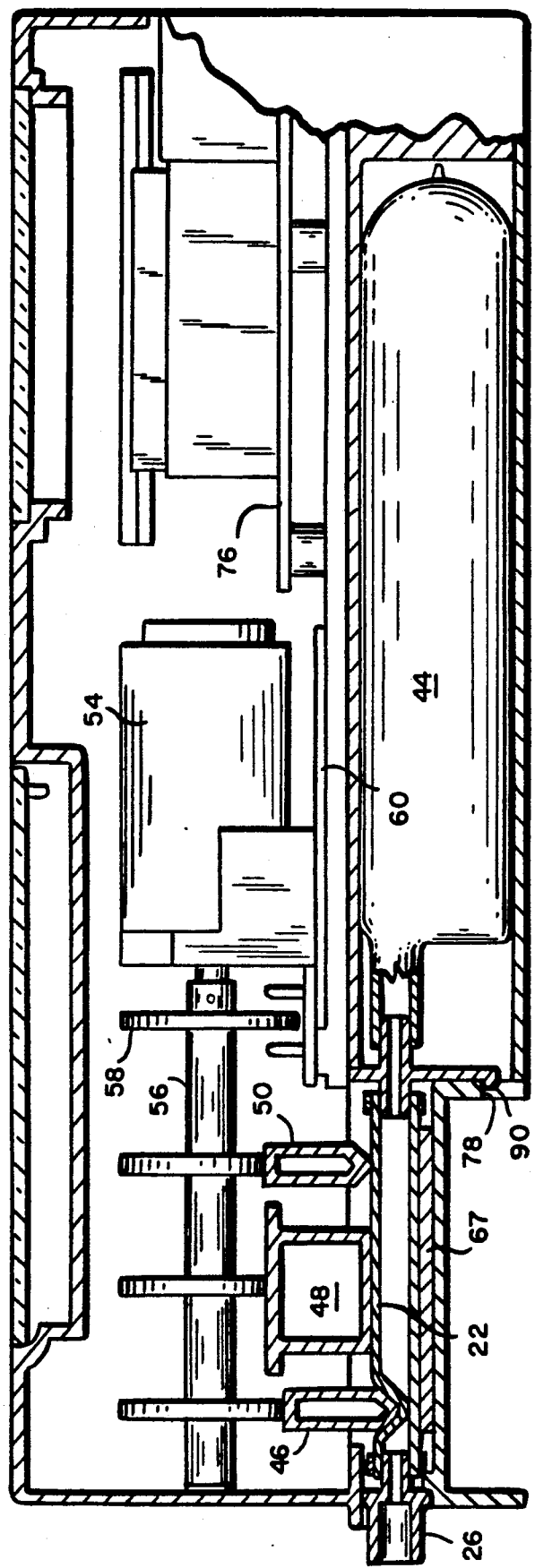
FIG. 5 is a side cross-sectional view of a pump and the cartridge of the present invention.

Referring now to FIGS. 3 and 5, the presently preferred pump for use with the present invention is provided with a plurality, four in this case, of linear peristaltic pumps. The illustrated pump is a three finger pump, called such because of the three cams which are repeatedly lowered and raised to provide the desired pumping action Each pump thus activates three cam followers, including an output valve 46, a pump plunger 48 and an input valve 50. Power for the pump is provided by a battery pack which may be loaded into a cavity behind a battery cover 52 alongside the peristaltic pumps within the housing 10. Each pump is provided with its own motor 54 which turns a cam shaft 56. The cam shaft 56 is provided with a timing disk or encoder 58. The timing disk is solid except for a sector which is removed. The disk can thus be read by an optical timing circuit on a printed circuit board 60 to count the rotations, thereby controlling the rate and location of the cam shaft 56.

To maintain improved accuracy, the cam followers should be made to always press against the tube 22, even when in the open position. The pump tube 22 is supported relative to the cam followers by a rigid base 67. The action of the fulcrum in the cartridge 20 ensures that the rigid base 67 is always positioned a fixed distance from the cam followers on the pump.

Pumping is performed as follows. With the pump plunger 48 and the input valve 50 retracted, the output valve 46 is lowered to close off the fluid conduits This permits the pump tube 22 to fill with fluid. This is the preferred position whenever the pump is inactive. Next, the input valve 50 is lowered to close off the pump tube 22 and prevent fluid from flowing back into the fluid source 44. The cam shaft is then turned permitting the tube 22 to expand, pushing the output valve 46 to open.

The pump plunger 48 is activated by the cam shaft to push fluid out of the tube 22 and through the outlet 26. Then the output valve 46 is again closed. The pump plunger 48 and the input valve 50 are permitted to open, thereby allowing the pump tube to refill with fluid. Thus, fluid is pumped out of the fluid source. The pump tube in the presently preferred embodiment has an inner diameter of 0.030 inches, an outer diameter of 0.156 inches and a 50 durometer Shore A. The rate of pumping is controlled by knowing the precise volume pumped in each cycle and monitoring the number of pumping cycles per unit of time.

A programmable microprocessor is provided on a control circuit board 76. Each of the four pump motors is controlled by the controller board 76. Since each fluid source has its own pump and pump motor, the rate and sequence of fluid infusion is entirely flexible. Infusions may take place concurrently or sequentially and at any rate. The desired sequence and rates of infusion are programmed into the controller board 76 through the programming jacks 16. Thus, in accordance with the present pump, multiple fluid infusion treatments may be delivered to a patient in any number of sequences and rates. Thus, the pump provides physicians with great latitude for selecting multiple-fluid drug regimens for treating patient illnesses.

Figure 6:
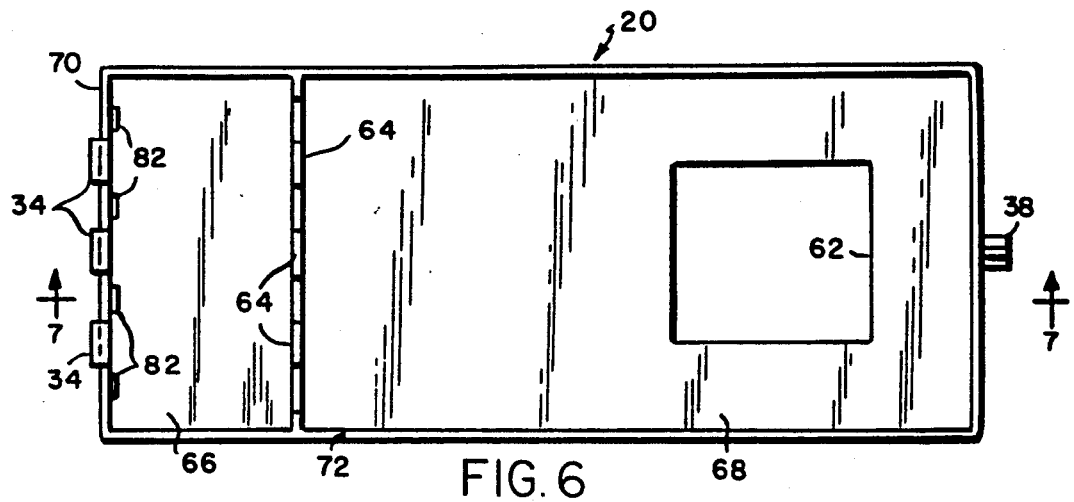
FIG. 6 is a plan view of a cartridge of the present invention.
Figure 7:
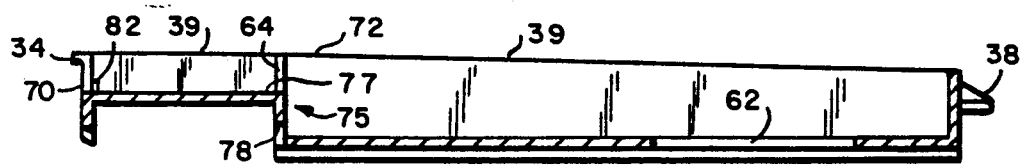
FIG. 7 is a side elevational view of the cartridge of FIG. 6.
Figure 8:
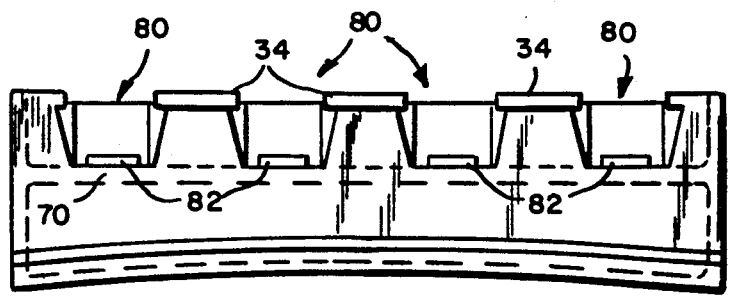
FIG. 8 is an elevational view of the cartridge of FIG. 6 taken along lines 8—8.
Figure 14:
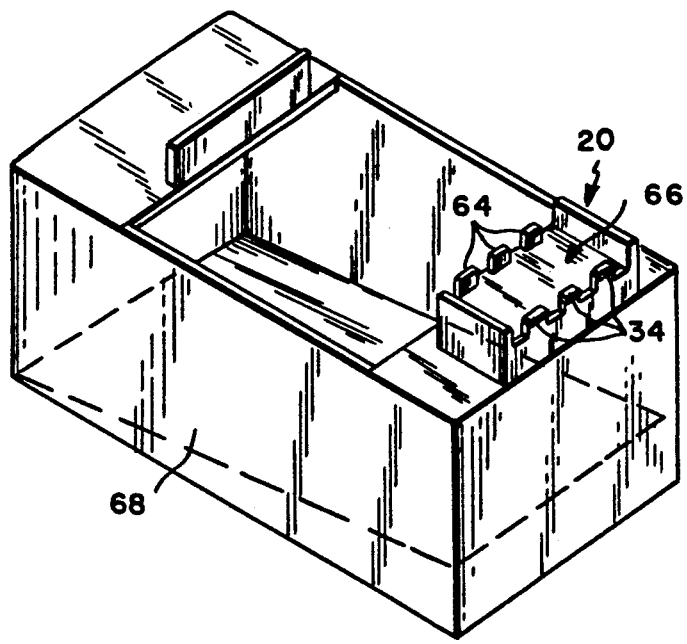

Referring now to FIGS. 6-8, the cartridge 20 of the present invention shall be described in greater detail. FIG. 6, illustrates a cartridge 20 of the type with a window 62. The window provides a hole through which lumens can be fed to connect the pump tubes 22 with fluid sources. A discontinuous dividing wall 64 separates the cartridge 20 into a pump interface portion 66 and a fluid source portion 68. The fluid source portion 68 may provide fluids through a window such as that shown in FIG. 6. Alternatively, the fluid source portion 68 may be filled with fluid source pouches 44. With the pouches 44, the cartridge 20 can be used by an ambulatory patient. The cartridge 20 with a window 62 permits the same pump apparatus to be used by a hospital in-patient. Alternatively, the fluid source portion 68 of the cartridge 20 can be made extra deep, as shown in FIG. 14, to provide room for a drug solution mini-bag. Such a mini-bag provides more volume of fluid than the pouches 44. The mini-bag of FIG. 14 incudes an inclined floor to help urge the fluid in the mini-bags towards the opening in the bottom of the bag. As such, the pump apparatus can be used with the mini-bags to provide a portable infusion apparatus which can be used by a patient undergoing high fluid volume infusions in the home.

The tabs 34 secure one end of the pump interface portion of the cartridge flat against the pump. The top edge of the cartridge 20 is flat from at least the front end wall 70 to the dividing wall 64. Just beyond the dividing wall 64 in the fluid portion of the cartridge, a fulcrum 72 is formed by bevelling the top edge of the cartridge from the fulcrum down towards a rear wall 74 of the cartridge. In accordance with the presently preferred embodiment of the present invention, the bevelling results in a drop off of 40 thousands of an inch from the top edge 39 at the dividing wall 64 down to the top edge 39 of the end wall 74. When the cartridge 20 is inserted into a pump, the tabs 34 support one end of the cartridge securely within the pump. The person inserting the cartridge pushes the rear end of the cartridge against the pump so as to be able to close the latch 36 to engage a tab 38 on the rear end 74 of the cartridge. The latch 36 on the pump is turned by a key to swing it onto the tab 38. The latch 36 lifts the tab 38 up towards the pump. In the latched position, the top edge of the cartridge 20 at the end wall 74 is 20 thousands of an inch away from the pump. Thus, the locked latch 36 applies pressure against the rear end of the cartridge to bend it upwards 20 thousands of an inch from its resting position. The tension travels back to the fulcrum 72 and forces the fulcrum flush against the pump. Thus, all of the bending of the cartridge 20 caused by the 20 thousandth displacement appears in the fluid source portion. Consequently, with the fulcrum in a known repeatable position, the pump interface portion on the other side of the fulcrum is properly spaced relative to the pump and accurately positioned every time the cartridge is inserted.

Also shown in FIG. 7 is a ledge 75 formed by the dividing wall 64. The ledge 74 has an upper edge 77 at the level of the base of the pump interface portion of the cartridge. The ledge 75 has a lower edge 78 or a series of individual lower edges 78 which are provided for engaging the pump tube mounts.

The end wall 70 has a series of uniquely shaped openings 80 which accommodate the outlet ends of the pump tube mounts. Immediately behind each opening 80 is a retaining stump 82. The opening 80 is shaped to secure the front wall of the pump tube mount in two directions. The front wall is prevented from moving up and down or left and right when installed within the cartridge opening 80 Furthermore, the opening 80 is given a unique shape as if it were a lock for a key. Just as a key may be uniquely designed to fit into a lock, the front wall of a pump tube mount can be uniquely shaped to fit the unique shape of the opening 80. This feature helps to ensure that only the appropriate tube mounts are inserted into the cartridge. The retaining stump 82 prevents the wall from moving back into the cartridge. The final direction of freedom is secured by the interaction of the rear wall of the pump to mount with the ledge 75 of the cartridge.

The front wall 84 of a pump tube mount can be seen in FIG. 9. Extending from the front wall 84 is an outlet 26 which is preferably a female luer connector. Two side walls 86 connect the front wall 84 to a rear wall 88. The rear wall 88 of the pump tube mount extends downward below the base 67 of the pump tube mount. At the lower end of the rear wall 88 are a pair of tabs 90 which engage the lower edge 78 of the ledge 75 in the cartridge 20. The dividing wall 64 in the cartridge 20 is discontinuous providing openings for each of the pump tube mounts. Also illustrated in FIG. 9 is a bag spike 92, which is inserted into a bag of fluid solution hanging from a pole to connect the pump with the fluid solution.

FIG. 10 shows how a pump tube mount of the present invention is inserted into a cartridge of the present invention. The rigid base 67 beneath the pump tube 22 does not extend all the way to the front wall or the rear wall. At the front wall, this provides a space into which the retaining stump 82 can be extended. Thus, the first step, is to position the front wall 84 up against the stump 82. The rear wall 88 is then lowered over the ledge 75 in the cartridge 20. As the rear wall 88 is lowered, the front wall 84 pivots into place within the opening 80. The rear wall 88 is lowered until the tabs 90 snap into the openings beneath the lower edge 78. The rear wall 88 is located so as to fit snugly against the ledge 75. Thus, when the tabs 90 have not yet been lowered into the openings beneath the edge 78, the tabs 90 are forcing the rear wall 88 away from its normal resting position.

Once the tabs get beneath the lower edge 78, the rear wall 88 is free to resume its resting position and therefore springs back against the ledge to make a snapping noise. The snap can be heard and felt so as to reassure the user that the pump tube mount is correctly positioned. The engagement of the tabs and the lower edge 78 keeps the pump tube mount in its correct position When in place, the rear wall 88 against the ledge 75 prevents the pump tube mount from moving forward. Thus, in combination with the retaining stump 80 and the opening 88, the pump tube mount is securely held in a known position in three dimensions.

Figure 11:
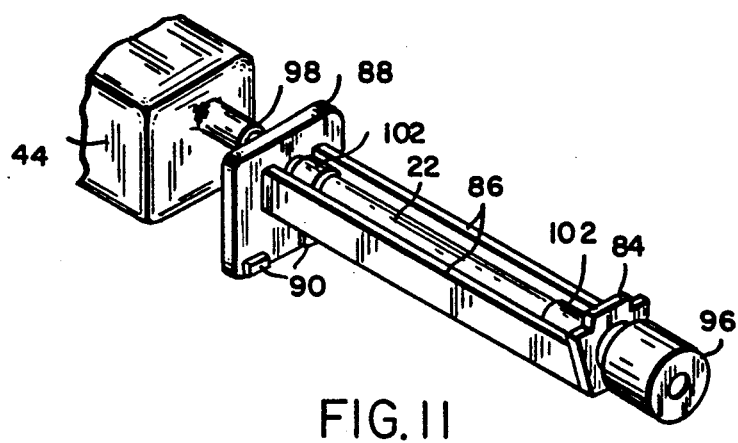
FIG. 11 is an isometric view of the pump tube mount of the present invention attached to a fluid source pouch.

FIG. 11 illustrates a disposable pump tube mount of the present invention The pump tube mount shown is attached to a flexible fluid source pouch 44. The fluid source pouch 44 may be adhesively bound to an inlet 94 extending from the rear wall 88 of the pump tube mount. A luer cap 96 may be screwed on to the luer connector 26 when the tube mount is not hooked up to an output line.

Figure 12:
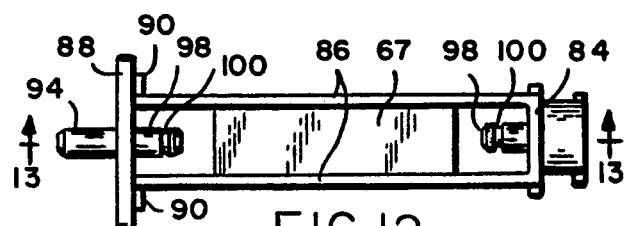
FIG. 12 is a plan view of the pump tube mount of the present invention without the tube and its retaining rings.

In FIG. 12, the pump tube mount is shown without a tube 22. Extending inwards from the front wall and the rear wall 88 is a fitting 98. The fitting 98 has a cylindrical exterior portion which makes surface contact with the inner circumference of the tube 22. The surface contact provides a frictional force between the fitting 98 and the inner circumference of the tube 22. In certain applications, this frictional force may be sufficient to hold the tube on the fittings. Since it is desirable in an infusion pump application to use a compressible material for the tube 22 which does not adhere to the fluids being delivered, it is often also true that such materials do not adhere to adhesives. Therefore, adhesive bonding is not a suitable means for attaching the tube to the fitting.

The presently preferred material for the tube 22 is Dow Corning medical-grade silicone.

In accordance with the present invention, an indentation such as an annular groove 100 is made in the cylindrical fitting 98. If the tube 22 fits tightly enough over the fitting 98, the silicone will slightly extend into the groove 100. This will provide an edge against the fitting which will hold the tube in place. To ensure that the silicone is depressed into the groove 100, a collar 102 may be placed over the tube concentrically aligned with the groove 100. The engagement of the tube with the groove provides adequate resistance against the shear forces created by the pumping action. The collar 102 is preferably a rigid material which is sized to compress the silicone into the groove 100. The collar 102 may be made from a material such as PVC.

Figure 13:
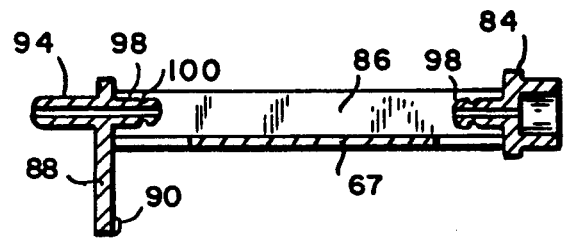
FIG. 13 is an elevational view of the pump tube mount of FIG. 12.

Referring now to FIG. 13, the rigid base 67 is shown. The base 67 is supported by the sidewalls 86 of the pump tube mount. As can be seen in FIG. 13, there is a space between the rigid base 67 and the front wall 84 into which the stump 82 can extend.

The pump tube mount advantageously provides a means for securing a silicone tube to a fitting without adhesive or outwardly projecting ridges which may subject the silicone to tearing. The mount is accurately positioned within the cartridge in three dimensions. Moreover, the fulcrum of the cartridge ensures accurate spacing between the pump and the pump interface portion of the cartridge to permit accuracy in infusion pump rates.

Of course, it should be understood that various changes and modifications to the preferred embodiment described above will be apparent to those skilled in the art. For example, any number of different front wall shapes and corresponding openings may be used in the front end wall of the cartridge to achieve the two dimensional accuracy of the present invention. Also, the cartridge of the present invention need not be restricted to use with four pump tube mounts, any number may be provided including a single fluid cartridge and pump. These and other changes can be made without departing from the spirit and scope of the invention and without diminishing its attendant advantages. It is therefore intended that such changes and modifications be covered by the following claims.

We claim:

1. A pump tube mount comprising:
    a front wall having a hollow outlet extending therefrom;
    a rear wall having a hollow inlet;
    means for connecting said front wall to said rear wall at a fixed distance from one another;
    a tube mounted between said front wall and said rear wall to provide fluid communication between the hollow outlet and the hollow inlet;
    a rigid base portion supported by said connecting means beneath said tube and spaced apart from said front wall; and
    said rear wall extending downwards below the level of said rigid base portion and having tabs extending from the rear wall beneath said rigid base portion projecting forwards from the rear wall.

2. The pump tube mount of claim 1 wherein said tabs cause said rear wall to make a snapping noise when the mount is properly installed.

3. The pump tube mount of claim 1 wherein said front wall is shaped so as to securely fit into a mating opening in a fluid source cartridge.

4. The pump tube mount of claim 1 further comprising:
    two elongated fittings, one extending from said front wall and the other extending from said rear wall, each of said fittings having a cylindrical exterior portion and an indentation in said exterior portion;
    said tube being mounted on said fittings such that the exterior portion of each of said fittings makes surface contact with an inner circumference of said tube; and
    two collars surrounding said tube, each at a position concentrically aligned with the indentation in one of said fittings.

5. The pump tube mount of claim 4 wherein the indentation in each of said fittings comprises an annular groove.

6. The pump tube mount of claim 4 wherein said tube is made of silicone.

7. The pump tube mount of claim 4 wherein said collars surround said tube tightly enough to force the inner circumference of said tube at least slightly into the indentations aligned with said collars.

8. A fluid source cartridge comprising:
    a housing having two end walls connected by two sidewalls and providing a pump interface portion at one end and a fluid source portion at the other end, said sidewalls each having a top edge with a bevel so as to form a fulcrum between the pump interface portion of said housing and the end wall at the fluid source portion; and
    means for engaging said cartridge with a pump extending from each of said two end walls.

9. The fluid source cartridge of claim 8 wherein said pump interface portion of said housing contains a compressible tube located above a rigid base.

10. The fluid source cartridge of claim 8 wherein the end wall in said pump interface portion has an opening shaped so as to mate securely with a similarly shaped wall on a pump tube mount.

11. The fluid source cartridge of claim 10 further comprising a retaining stump adjacent said opening to hold the wall of said pump tube mount in the opening.

12. The fluid source cartridge of claim 11 further comprising a ledge located near the fulcrum made by said sidewalls, said ledge having an upper edge and at least one lower edge such that when a rear wall of said pump tube mount is lowered over said ledge, tabs on said rear wall snap into said at least one lower edge.

13. The fluid source cartridge of claim 8 wherein said engaging means comprises a tab extending from the end wall at said fluid portion and three tabs extending from the top edge of the end wall at said pump interface portion.

14. A fluid source cartridge comprising:
 a housing having a pump interface-portion and a fluid source portion, said pump interface portion having a top edge for lying flat against a pump and said fluid source portion having a top edge with one end adjacent the top edge of said pump interface portion and an other end where the edge is lower relative to the top edge of said pump interface portion;
 means attached to said pump interface portion for interengaging a pump; and
 means extending from said fluid source portion proximate to the other end of said top edge for making engagement with a latch member on said pump, such that when engaged said fluid source portion is bent towards said pump to hold said pump interface portion securely in position.

15. A fluid source cartridge comprising:
 a housing with a pump interface portion having an end wall with an opening for mating with a front wall in a pump tube mount such that when mated said front wall is securely positioned in two dimensions within said opening;
 a retaining stump in said housing to prevent said front wall of said mount from sliding into the housing and out of mating engagement with the end wall; and
 a ledge in said housing against which a rear wall on said pump tube mount lies flat to prevent said front wall of said mount from sliding out of the housing, said ledge including a lower edge into which a tab on said rear wall extends to hold said rear wall in place.

16. The fluid source cartridge of claim 15 wherein said housing comprises a fulcrum located between said pump interface portion and an other end wall of housing.

17. The fluid source cartridge of claim 16 wherein said housing includes two sidewalls connecting the end wall with the other end wall and wherein said fulcrum is formed on said two sidewalls.

* * * * *